United States Patent [19]

Dalton et al.

[11] Patent Number: 4,683,310

[45] Date of Patent: Jul. 28, 1987

[54] PYRIDINE DICARBOXYLIC ESTER METAL EXTRACTANTS

[75] Inventors: Raymond F. Dalton, Cheshire; Raymond Price, Huddersfield; Peter M. Quan, Lancashire; David Stewart, Oldham, all of England

[73] Assignee: Imperial Chemical Industries, PLC, England

[21] Appl. No.: 702,579

[22] Filed: Feb. 19, 1985

Related U.S. Application Data

[60] Division of Ser. No. 418,833, Sep. 16, 1982, Pat. No. 4,525,330, which is a continuation-in-part of Ser. No. 341,176, Jan. 20, 1982, abandoned.

[30] Foreign Application Priority Data

Feb. 3, 1981 [GB] United Kingdom ................ 8103223
Aug. 26, 1981 [GB] United Kingdom ................ 8126079

[51] Int. Cl.$^4$ ............................................. C07D 213/80
[52] U.S. Cl. ......................................... 546/321; 546/8
[58] Field of Search ..................................... 540/321, 8

[56] References Cited

U.S. PATENT DOCUMENTS 2,809,197 10/1957 Kruse ...................................... 546/2
4,552,632 11/1985 Andersen et al. ..................... 423/24

Primary Examiner—Henry R. Jiles
Assistant Examiner—Dale A. Bjorkman
Attorney, Agent, or Firm—Cushman, Darby & Cushman

[57] ABSTRACT

Metal values are extracted from aqueous solutions of metal salts containing halide or pseudo halide ions by pyridine derivatives containing the substituent —(COX)$_A$ where X is the group —OR$_1$ or —NR$_2$R$_3$ and n is 1, 2 or 3. R$_1$ is a hydrocarbyl group containing from 5 to 36 carbon atoms and R$_2$ and R$_3$ are hydrogen or a hydrocarbyl group wherein R$_2$ and R$_3$ together contain from 5 to 36 carbon atoms. The process is especially useful for the recovery of metals from leach solutions derived from sulphur-containing ores such as chalcopyrite.

8 Claims, No Drawings

PYRIDINE DICARBOXYLIC ESTER METAL EXTRACTANTS

This is a division of application Ser. No. 418,833, filed Sept. 16, 1982, now U.S. Pat No. 4,525,330 which in turn is a continuation-in-part of application Ser. No. 341,176, filed Jan. 20, 1982, now abandoned This invention relates to a process for the extraction of metal values from aqueous solutions of metal salts, and in particular to a process for the extraction of metal values from aqueous solutions in the presence of halide anions.

The use of solvent extraction techniques for the hydrometallurgical recovery of metal values from metal ores has been practised commercially for a number of years. For example copper may be recovered from oxide ores or from ore tailings by treating the crushed ore with sulphuric acid to give an aqueous solution of copper sulphate which is subsequently contacted with a solution in a water-immiscible organic solvent of a metal extractant whereby the copper values are selectively extracted into the organic solvent phase.

The application of solvent extraction techniques to aqueous solutions containing halide ions however has hitherto presented numerous technical problems.

Of particular importance in this connection is the development of hydrometallurgical routes (as an alternative of smelting) for the extraction of metal values from sulphur-containing ores such as chalcopyrite. Such ores may be leached for example using ferric chloride or cupric chloride solutions, but the solvent extraction of the resultant leach solution presents formidable difficulties.

The present invention provides a process for the extraction of metal values from aqueous solutions containing halide ions by the use of metal extractants whose several properties meet the stringent requirements imposed on the extractant by the system.

According to the present invention there is provided a process for extracting metal values from aqueous solutions of metal salts containing halide or pseudo halide anion which comprises contacting the aqueous solution with a solution in a water-immiscible organic solvent of a substituted pyridine of formula:

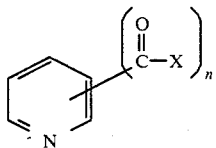
(I)

wherein X is the group $-OR_1$ or $-NR_2R_3$, $R_1$ being a hydrocarbyl group containing from 5 to 36 carbon atoms and $R_2$ and $R_3$ being hydrogen or a hydrocarbyl group, $R_2$ and $R_3$ together containing from 5 to 36 carbon atoms, and n is 1, 2 or 3.

When n is 2 or 3, the substituent $-X$ in the respective groups $-COX$ may be the same or different. For example, when n is 2, the two groups $-COX$ may be $-COR_1$ and $-COR_1'$ respectively where $R_1$ and $R_1'$ are both hydrocarbyl groups containing from 5 to 36 carbon atoms. Similarly, when n is 2, the two groups $-COX$ may be $-COR_1$ and $-CONR_2R_3$ respectively.

According to a further aspect of the present invention there is provided a process for extracting metal values from aqueous solutions of metal salts containing halide or pseudo halide anion which comprises contacting the aqueous solution with a solution in a water-immiscible organic solvent of a 3- or 4-substituted pyridine of formula:

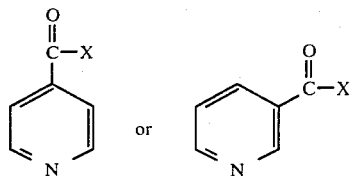

wherein X is the group $-OR_1$ or $-NR_2R_3$, $R_1$ being a hydrocarbyl group containing from 5 to 36 carbon atoms and $R_2$ and $R_3$ being hydrogen or a hydrocarbyl group, $R_2$ and $R_3$ together containing from 5 to 20 carbon atoms.

According to a further aspect of the present invention there is provided novel metal extractants. Thus there is provided a 3- or 4-substituted pyridine of formula

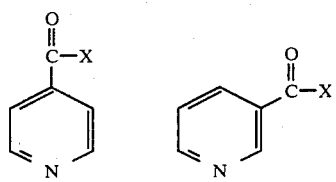

wherein X is the group $-OR_1$ or $-NR_2R_3$, $R_1$ being an alkyl group containing from 9 to 24 carbon atoms and having the formula

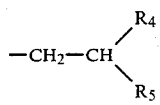

wherein $R_4$ and $R_5$ are alkyl groups, and $R_4$ contains two fewer carbon atoms than $R_5$, and $R_2$ and $R_3$ together containing a total of from 15 to 36 carbon atoms, provided that when $R_2$ is hydrogen, $R_3$ is a branched chain alkyl group.

There is also provided a substituted pyridine of formula:

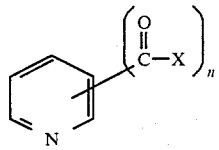

wherein X is the group $-OR_1$ or $-NR_2R_3$, and n is 2 or 3, the respective groups $R_1$ being alkyl groups containing a total of from 16 to 36 carbon atoms, and the respective groups $R_2$ and $R_3$ being alkyl groups wherein the total number of alkyl carbon atoms contained in all the respective groups $R_2$ and $R_3$ is from 20 to 70.

The pyridine ring may carry substituents in addition to the group(s) $-COX$. Examples of suitable substituents are halogen groups, alkyl groups, aryl groups, alkoxy groups, aryloxy groups, aralkyl groups, cyano groups and nitro groups. The pyridine ring may also carry a carboxylic acid group, and the invention includes for example a half ester of a pyridine dicarboxylic acid.

Substitution in the pyridine ring may for example result from the method of synthesis. For example bis ester of 4-phenylpyridine-3,5-dicarboxylic acid may be prepared from methyl propiolate, aromatic aldehydes and ammonium acetate in acetic acid followed by oxidation to the pyridine derivative and ester exchange (Chennat and Eisner, J. C. S. Perkin I, 1975).

When n is 1, examples of compounds which may be used in the process of the invention include esters or amides of nicotinic acids, isonicotinic acids and picolinic acids. When n is 2, examples of compounds which may be used in the process of the present invention include bis esters or amides of pyridine-2,4-dicarboxylic acid, of pyridine-2,5-dicarboxylic acid, and of pyridine-3,5-dicarboxylic acid. When n is 3, examples of compounds which may be used in the process of the present invention include tris esters or amides of pyridine-2,4,6-tricarboxylic acid. Mixtures of such compounds may be used, for example a mixture of bis esters or amides of isomeric pyridine-dicarboxylic acids.

The substituted pyridines of the present invention wherein X is the group $-OR_1$ may be prepared by conventional means, for example by the reaction of a pyridine carboxylic acid, for example isonicotinic acids, nicotinic acids or picolinic acids respectively with the appropriate alcohol to form the desired esters. Alternatively the lower esters, for example methyl or ethyl esters may be subjected to ester exchange reactions with higher alcohols, or the acid chlorides may be reacted with the appropriate alcohol or phenol. Dicarboxylic acid esters of pyridine may conveniently be prepared from lutidines, for example by oxidation and esterification.

$R_1$ may for example be an alkyl group, for example an octyl, nonyl, decyl, dodecyl, tridecyl, pentadecyl, hexadecyl or octadecyl group or substituted alkyl group, for example a group containing one or more propylene oxide residues formed by reacting propylene oxide with an alcohol before esterification to give the substituted pyridine; $R_1$ may be a cyclo alkyl group such as cyclohexyl; $R_1$ may be an aralkyl group such as benzyl; or $R_1$ may be an aryl, alkylaryl or alkoxyaryl group for example p-nonylphenyl or p-dodecylphenyl.

When n is 1 and there is no other substituents in the pyridine ring, $R_1$ is preferably a branched chain alkyl group containing from 9 to 24 carbon atoms.

$R_1$ may be an isomeric mixture of groups containing the same number of carbon atoms or a mixture of groups containing different numbers of carbon atoms (which may themselves be an isomeric mixture), for example a mixture of different alkyl groups, If $R_1$ is a mixture of groups containing different numbers of carbon atoms, the average number of carbon atoms is preferably from 9 to 24.

Highly branched groups $R_1$ may usefully be obtained by the reaction of the pyridine carboxylic acid with alcohols prepared by the Guerbet and Aldol condensations. Such alcohols are characterised by branching at the position beta to the hydroxyl group, and have the general formula:

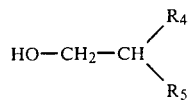

In general $R_4$ contains 2 fewer carbon atoms than $R_5$, and groups $R_1$ derived from these alcohols include for example,

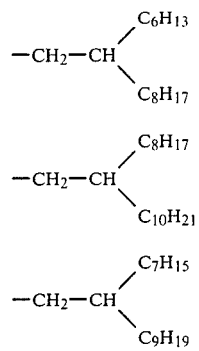

$R_4$ and $R_5$ may be straight chain or branched chain alkyl groups and may be isomeric mixtures of alkyl groups. A mixture of highly branched alcohols may be obtained by Guerbet or Aldol condensations of mixtures of alcohols and aldehydes respectively.

Excellent solubility is conferred upon the compounds of formula I where the alcohol is the product of the aldol dimerisation of commercial nonaldehyde. In this alcohol the group $R_1$ is believed to consist essentially of a mixture of geometrical isomers of a radical of the formula:

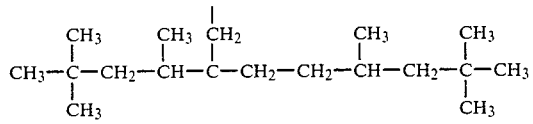

When n is 2, the respective groups $R_1$ ($R_1$ and $R_1'$) may be any of those groups $R_1$ listed previously. $R_1$ and $R_1'$ are conveniently the same and are preferably straight chain or branched chain alkyl groups. When n is 2, we have found that to achieve the desired solubility of the metal complex in preferred solvents, $R_1$ and $R_1'$ preferably together contain a total of from 16 to 36 carbon atoms. The groups $R_1$ may contain a mixture of isomers, for example a mixture of nonyl isomers derived from isononanol obtained by the hydroformylation of a mixture of octenes, a mixture of decyl isomers obtained from isodecanol, or a mixture of tridecyl isomers obtained from tridecanol.

The substituted pyridines of the present invention wherein X is the group $-NR_2R_3$ may be prepared by conventional means, for example by reaction of pyridine carboxylic acids and their lower esters with higher primary or secondary amines. Alternatively the acid chloride of the pyridine carboxylic acid may be reacted with the appropriate amine.

The amide group $-NR_2R_3$ may be primary ($R_2$ is hydrogen) or secondary. $R_2$ and $R_3$, which may be the same or different may be groups of the type indicated above for $R_1$. $R_2$ and $R_3$ taken together contain from 5 to 36 carbon atoms. Thus $R_2$ may be for example a lower alkyl group, for example a methyl group, provided $R_3$ is correspondingly larger. $R_2$ and $R_3$ taken together are preferably alkyl groups containing a total of 15 to 36 carbon atoms. For secondary amides sufficient solubility in preferred organic solvents may generally be achieved if $R_2$ and $R_3$ are straight chain or branched chain alkyl groups. However for primary amides ($R_2$ is hydrogen), $R_3$ is preferably a branched chain alkyl group. When n is 2, and the groups $R_2$ and $R_3$ are all alkyl groups, the total number of alkyl carbon atoms preferably does not exceed 70, for example the total number of alkyl carbon atoms is preferably from 20 to 70.

The process of the present invention may be applied to the extraction from aqueous solutions containing halide or pseudohalide ion of any metal capable of forming a stable halide- or pseudohalide-containing complex with the pyridine derivative in the water-immiscible organic solvent. Examples of such metals include copper, cobalt, cadmium and zinc. The process of the present invention is especially applicable to the solvent extraction of copper from aqueous solutions obtained by the halide or pseudo halide leaching of sulphur-containing copper ores, for example from solutions obtained by the leaching of ores such as chalcopyrite with aqueous ferric chloride or cupric chloride solutions.

The leaching of ores such as complex sulphide ores, for example chalcopyrite with for example aqueous ferric chloride solution containing hydrochloric acid gives rise to leach solutions containing cuprous and cupric ions, ferrous and ferric ions and excess chloride anion. The ratio fo cuprous to cupric ion depends on the leach conditions selected. The sulphur content of the ore may be precipitated as elemental sulphur. Whilst the scope of the present invention is not to be taken as being limited to the treatment of any particular halide-containing aqueous solution, typical solutions obtained by the leaching of chalcopyrite with acidified ferric chloride may contain between 10 and 60 grams per liter of copper, between 50 and 150 grams per liter of iron, may typically be between 0.1M and 1M hydrochloric acid and may be between about 2M and 8M in total chloride ion. Certain leach systems may give total chloride ion contents as high as 10M or 12M. All leach solutions encountered in practice will also contain varying quantities of the many other metals present in the ore body. Certain leach solutions may contain high levels o specific metals, for example zinc, in addition to copper. copper.

It will be appreciated that the process of the present invention may be incorporated into a wide variety of different methods for the overall recovery of metals from their ores or from other metal-bearing sources. Details of these methods will vary depending on the metal concerned and the nature and composition of the leach solution. Whilst the process of the present invention is not limited to any single overall method for the recovery of metals, the stringent conditions imposed on the pyridine extractant are best illustrated if the solvent extraction process is seen as a step in an integrated process of the recovery of the metal from the ore. For example an integrated process which is especially suitable for leach solutions containing high level of cupric ion comprises the following steps:

1. Leaching of the ore with aqueous ferric or cupric chloride solutions, and removing the elemental sulphur produced;

2. Contacting the leach solution from step 1 (in which the ferric ion is at least partially reduced to ferrous ion) with a solution in a water-immiscible solvent of the extractant, whereby the copper is transferred into the organic phase in the form of a chloride-containing complex with the extractant;

3. Separating the organic phase containing the complex of copper with the extractant from the aqueous phase containing the ferric/ferrous chloride;

4. Contacting the organic phase from step 3 with an aqueous strip solution which is water, or which contains a reduced concentration of chloride ion, whereby the chloride-containing complex of copper with the extractant is unstable and copper transfers into the aqueous strip solution;

5. Separating the organic phase containing the stripped extractant from the aqueous strip solution containing the copper chloride; and 6. Electrolysing the strip solution from step 5 to recover copper. The electrolysis step is suitably arranged such that oxidation of ferrous ion with transfer of chloride ion takes place in the anode compartment, such that the solution leaving the cathode compartment is denuded in both copper and chloride ion. Alternatively chlorine gas may be evolved at the anode and optionally used as oxidant to regenerate the leach solution.

In order to preserve the overall stoichiometry of the sequence of reactions, it may be necessary to provide additional oxidation of ferrous to ferric ion, and to remove the iron entering the system continuously from the chalcopyrite ($CuFeS_2$), for example in the form of iron oxide such as geothite.

For a fully integrated process it is highly desirable that the solutions be re-circulated between the various stages. Thus aqueous strip solution used in step 4 is preferably derived from the electrolysis step 6 and is preferably the solution leaving the cathode compartment denuded in both copper and chloride ion. Similarly the organic phase containing the stripped extractant which is separated in step 5 is preferably re-circulated to the extraction stage 2. The ferric chloride solution derived from the electrolysis step 6 may be returned for further leaching of the ore.

Considering first the extraction stage 2 and the strip stage 4, the extraction of for example cupric ion by the extractant may be represented by an equation such as the following:

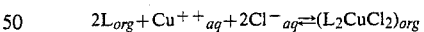

$$2L_{org} + Cu^{++}{}_{aq} + 2Cl^-{}_{aq} \rightleftharpoons (L_2CuCl_2)_{org}$$

This equation is a grossly oversimplified representation of a very complex process and is not to be taken as in any way limiting the scope of the present invention, but it serves to illustrate the formation of a neutral organic phase complex of copper and the extractant (L) which is believed to predominate in the process of the present invention. Other equations may be used to represent the extraction and stripping of cuprous ion or of other metals by the extractant.

The above equation assumes that the extractant acts as a monodentate ligand, and whilst this is believed to be generally true, esters and amides of 2-carboxypyridines do at least have the potential of acting as bidentate ligands. Under certain conditions other species, for example oligomeric complexes such as $L_2(CuCl_2)_n$ may be formed. The formation of oligomeric species is generally undesirable since the efficiency of copper extraction is reduced and in addition the oligomeric complexes tend to have a low solubility in organic solvents. We have found that the tendency to the formation of oligomeric species is especially low with esters and amides of 2-carboxypyridines.

The equation also illustrates the reversible nature of the extraction, whereby the complex of copper and the extractant in the organic phase can be stripped on contact with water or with an aqueous solution containing a reduced chloride or a reduced copper content such that copper is transferred to the aqueous phase and the free extractant is at least partially regenerated in the organic phase.

Most efficient stripping will be obtained using water itself as the stripping medium, and the process of the present invention may be combined with a water stripping stage. However, it will be noted that in a fully integrated process, it is preferred that the loaded extractant be stripped with the solution derived from the electrolysis stage and denuded in copper and chloride ion. In an extreme case, the aqueous phase may be entering the electrolytic cell containing about 40 or 50 grams per liter copper and may leave it still containing as much as 30 grams per liter copper or more. The requirement that the extractant will be able to efficiently extract copper from the leach solution, whilst at the same time be stripped by a solution containing relatively high levels of copper is exacting. Preferred extractants for use in the process of the present invention are capable of being stripped by an aqueous solution containing relatively high levels of copper, for example from 20 to 35 grams per liter of copper.

Since the leach solution contains high levels of iron, it is clearly important that the extractant should have good selectivity for copper over iron. The extractants of the present invention have this property. Of particular importance in an integrated system, where the copper is recovered by electrolysis of the pregnant aqueous strip solution, is selectivity for copper over silver and other minor extractable constituents of the ore. The reason for this is that whilst metals such as zinc and cadmium are more electronegative than copper and are not electrodeposited with it, silver is both co-deposited with copper and furthermore adversely affects the physical properties of the copper so that an expensive electrorefining stage is required. Preferred extractants of the present invention have excellent selectivity for copper over silver under appropriate operating conditions.

A yet further property which is of importance for an extractant in the process of the present invention is the absence of significant protonation by the acidic leach liquor. Such protonation may be represented by an equation such as:

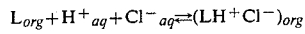

$$L_{org} + H^+{}_{aq} + Cl^-{}_{aq} \rightleftharpoons (LH^+Cl^-)_{org}$$

where L is the extractant. Such protonation of the ligand not only carries hydrochloric acid into the organic phase, building up unnecessary chloride concentration on the strip side, but is also believed to be associated with loss of selectivity for copper over silver and other trace components such as antimony and arsenic. Again the preferred extractants of the present invention have excellent resistance to protonation even in contact with relatively acidic leach solutions.

As illustrated by the Examples, the extractants of the present invention provide a range of properties so that the optimum extractant may be selected for a given leach solution. In particular, a "strong" extractant, for example, isooctadecyl nicotinate, is capable of extracting high levels of copper from a leach solution containing relatively low chloride ion content (for example about 3.7M) but tends to undergo undesirable protonation and acid transfer at higher acid/chloride ion concentrations (for example H+, 0.1M; Cl−, 9.8M). On the other hand, a "weak" extractant such as a diester of pyridine-2,5-dicarboxylic acid is found to transfer only low levels of acid, even from solutions concentrated in chloride ion and acid (for example 10.7M and 1M respectively). Furthermore the lower inherent ability of the extractant to transfer copper into the organic phase is offset by the improved transfer of copper at these higher chloride ion concentrations.

Bis esters of pyridine-3,5-dicarboxylic acids, for example the bis-nonyl ester, are weak extractants which furthermore show high selectivity for copper over zinc, and provide a potential for recovery of zinc in leach solutions containing high levels of both copper and zinc.

Examples of suitable water-immiscible organic solvents are aliphatic, aromatic and alicyclic hydrocarbons, chlorinated hydrocarbons such as perchloroethylene, trichloroethane and trichloroethylene. Mixtures of solvents may be used. Especially preferred in conventional hydrometallurgical practice are mixed hydrocarbon solvents such as high boiling, high flash point, petroleum fractions (for example kerosene) with varying aromatic content. In general, hydrocarbon solvents having a high aromatic content, for example AROMASOL H which consists essentially of a mixture of trimethylbenzenes and is commercially available from Imperial Chemical Industries PLC (AROMASOL is a registered trade mark), provide a higher solubility for the extractant and its copper complex, whilst kerosene having a relatively low aromatic content, for example ESCAID 100 which is a petroleum distillate comprising 20% aromatics, 56.6% paraffins and 23.4% naphthenes commercially available from ESSO (ESCAID is a registered trade mark) may in certain cases improve the hydrometallurgical performance of the extractant. Factors influencing the solubility of the extractant and its copper complex are complicated, but in general extractants having highly branched substituents and/or an isomeric mixture of substituents have comparatively high solubility.

We have found that isonicotinic acid derivatives and their copper complexes, for example (2-hexyldecyl)isonicotinate, have surprisingly high solubility in both high and low aromatic content hydrocarbon solvents.

The concentration of the extractant in the water-immiscible organic solvent may be chosen to suit the particular leach solution to be treated. Typical values of extractant concentration in the organic phase are between about 0.1 to 2 Molar, and an especially convenient range is from 0.2 to 0.8 Molar in the organic solvent.

The extraction stage and the strip stage of the solvent extraction process may conveniently take place at ambient temperature. However it is possible to improve net copper transfer from the leach solution to the strip solution if the extraction stage is operated at ambient temperature, whilst the strip stage is operated at elevated temperature, for example up to 50° C. We have also found that the undesirable formation and build-up of oligomeric complexes of the extractant and copper may be alleviated if the strip stage is operated at elevated temperatures, for example up to 50° C.

The invention is illustrated by the following Examples in which all parts and percentages are by weight unless otherwise stated.

EXAMPLE 1

(2-(n)Hexyldecyl)nicotinate was prepared as follows:

A stirred mixture of nicotinic acid (61.5 parts), dimethylformamide (0.63 parts) and xylene (174 parts) was heated to 80° below a condenser set for reflux. Thionyl chloride (65.5 parts) was then added during 1-2 hours, the temperature of the reaction mixture being allowed to rise to 90°-95° during the addition. The mixture was then stirred at 90°-95° for 3 hours. The condenser was then set for distillation and the temperature was raised until excess thionyl chloride had distilled and xylene had begun to distil. The mixture was then allowed to cool to 80°-85° and 2-(n)hexyldecanol (112 parts) was added during 30 minutes. The mixture was stirred at 80°-85° for 2 hours and was then cooled to room temperature, and extracted with a solution of sodium hydroxide (40 parts) in water (165 parts). The xylene solution was washed alkali free with more water, and the xylene was distilled under reduced pressure leaving (2-hexyldecyl)nicotinate [147 parts] as a brown oil. The purity was estimated at 95% by titration of a sample with N/10 perchloric acid in acetic acid medium. The compound was distilled, b.p. 176°-184° at 0.4 mm pressure, yielding 109 parts of straw-coloured liquid which was 98-99% pure.

The ability of (2-(n)hexyldecyl)nicotinate to extract copper from aqueous solution containing chloride ion was investigated.

An aqueous solution (A) was made up which was 0.1M in cupric chloride (6.35 gpl copper), and 0.1M in hydrochloric acid, and which contained in addition 250 g/liter of calcium chloride dihydrate. This solution was then agitated for 15 minutes with an equal volume of a solution (B) which was a 0.2M solution of (2-hexyldecyl)nicotinate in AROMASOL H. The layers were allowed to separate and settle, and were separately analysed for copper content. The percentage of the copper initially present in A which had passed into B, was 44.5%. The resultant loaded organic solution B was then stripped with an aqueous solution (C) which was 0.472M in cupric chloride, i.e. one which contained 30 gpl of copper. It was found that copper passed from the organic to the aqueous solution. The percentage of the copper originally present in A which had been transferred to solution C was 25.5%. The transfer of hydrochloric acid from solution A to soluion B was negligible.

Extraction of copper by the same extractant from a more strongly acidic solution was also examined. The same solutions and procedure as before were used, except that solution A was 1.0M rather than 0.1M hydrochloric acid. The percentage of copper extracted into the organic solution (B) and the percentage which finally passed into the aqueous solution of cupric chloride (C) were 47.8% and 30.6% respectively. The amount of hydrochloric acid which passed from solution A to solution B under these extremely acidic conditions was measured. Expressed as a percentage of that which would be transferred if every molecule of the ligand combined with one molecule of hydrochloric acid, the acid transfer was only 1.9%.

The above results are summarised in Table 1.

EXAMPLE 2

Tridecyl nicotinate was prepared using the method of Example 1 from commercial tridecanol (an isomeric mixture) and nicotinic acid. The product had a boiling point of 136° to 140° C. under 0.05 mm pressure and an estimated purity of 100% based on a molecular weight of 305.5.

The ester was evaluated as an extractant for copper from aqueous solution containing chloride ion using the method of Example 1.

The results are presented in Table 1.

EXAMPLE 3

N,N-di-(n)-octylnicotinamide was prepared using the method of Example 1 from nicotinic acid and di-(n)-octylamine. The product had a boiling point of 180° to 183° C. at 0.15 mm pressure and an estimated purity of 95.5%.

The amide was evaluated as an extractant for copper from aqueous solution containing chloride ion using the method of Example 1.

The results are presented in Table 1.

It will be noted that this compound is a stronger extractant than those shown in the previous Examples, and would be more suitably employed for the extraction and subsequent recovery of copper from an aqueous solution of lower concentration of chloride ion. It would also be preferable to strip the extractant with a strip solution which was lower in copper and/or in chloride ion than solution C.

EXAMPLE 4

(2-(n)-hexydecyl)isonicotinate was prepared using the method of Example 1 from isonicotinic acid and 2-hexyldecanol. The product had a boiling point of 180° to 190° C. at 0.75 mm pressure and an estimated purity of 97.5%.

The ester was evaluated as an extractant for copper from aqueous solution containing chloride ion using the method of Example 1.

The results are presented in Table 1.

TABLE 1

| Extractant | Transfer of copper (%) from 0.1 M HCl to B | Transfer of copper (%) from 0.1 M HCl to C | Transfer of copper (%) from 1.0 M HCl to B | Transfer of copper (%) from 1.0 M HCl to C | Acid co-extracted (%) from 1.0 M HCl to B |
|---|---|---|---|---|---|
| Example 1 | 44.5 | 25.5 | 47.8 | 30.6 | 1.9 |
| Example 2 | 44.6 | 26.2 | 47.6 | 29.8 | 3.3 |
| Example 3 | 72.2 | 15.2 | 68.2 | 11.2 | 18.8 |
| Example 4 | 51.0 | 23.8 | 57.0 | 31.4 | 3.0 |

*For all Examples the acid co-extracted from 0.1 M HCl to B was negligible.

EXAMPLE 5

A solvent extraction circuit was assembled consisting of small scale mixer settler units. The circuit comprised 3 stages of extraction and 2 stages of stripping and pumping was arranged such that over both the extraction and stripping parts of the circuit the organic and aqueous solutions flowed counter current wise.

The aqueous feed solution had the following composition of metals:

| | |
|---|---|
| Copper ($Cu^{2+}$) | 16.0 g per liter |
| Iron ($Fe^{2+}$) | 40.4 g per liter |

-continued

| Silver (Ag+) | 18.9 mg per liter |

In addition, the solution contained 150 g per liter of calcium chloride added as the dihydrate $CaCl_2.2H_2O$ and contained 3.6 g per liter of hydrochloric acid giving a total chloride ion concentration of 4.23 moles per liter.

The strip solution consisted of an aqueous solution containing 28.9 gpl copper as cupric chloride with no added acid.

The solvent phase comprised a 19.2% by weight solution (0.553 moles per liter) of the extractant of Example 1 dissolved in AROMASOL H.

The pumps and agitators in the circuit were started and the flow rates adjusted to give an organic flow of 33.3 ml/min and aqueous flows of 13.3 ml/min (2.5 to 1 organic to aqueous phase ratio).

After the circuit had been running successfully for 4 working days at an average temperature of 15° C., samples taken from the aqueous raffinate; from the extraction circuit; and of the pregnant strip solution were analysed.

The results obtained are summarised in Table 2.

TABLE 2

|  | $Cu^{2+}$ gpl | $Fe^{2+}$ gpl | $Ag^+$ mg/l (ppm) |
| --- | --- | --- | --- |
| Aqueous feed | 16.0 | 40.4 | 18.9 |
| Raffinate | 2.49 | 39.8 | 18.4 |
| Strip solution | 28.9 | 0.24 | 0 |
| Pregnant strip solution | 44.5 | 0.8 | 0.6 |

EXAMPLE 6

(2-(n)-Octyldodecyl)nicotinate was prepared from nicotinic acid and 2-(n)octyldodecanol using the general method of Example 1 with the following minor changes. The temperature after thionyl chloride addition was maintained at 80° C. for 2 hours, and after the esterification reaction, the solution was diluted with petroleum ether (60°-80° ), washed with water to remove acidity and the solvents removed by distillation. The product had a boiling range of 190°-200° C. at 0.05 mm mercury pressure and an estimated purity of 87.9%.

The ability of (2-(n)octyldodecyl)nicotinate to extract copper from aqueous solution containing chloride ion was investigated.

An aqueous solution (A) was made up which was 0.1M in cupric chloride (6.35 g/l copper), 0.1M in hydrochloric acid and contained 250 g/l of calcium chloride dihydrate, providing a total chloride ion concentration of 3.7M. This solution was shaken for 1 minute with an equal volume of a solution (B) which was a 0.2M solution of (2-(n)-octyldodecyl)nicotinate in ESCAID 100. The layers were allowed to separate, the aqueous layer was analysed for copper and the solvent layer for acid transferred with the copper. The percentage of copper initially present in A which had passed into B was 52%. There was no detectable transfer of hydrochloric acid into B.

These results are summarised in Table 3.

EXAMPLE 7

Iso-hexadecyl nicotinate was prepared from nicotinic acid and a commercial material, iso-hexadecyl alcohol, obtained from Farbwerke Hoechst AG. The general method of Example 1 was used except that the temperature after thionyl chloride addition was maintained at 80° C. for 2 hours, and after the esterification reaction the solution was cooled and washed with 0.5M sodium hydroxide, 0.5M hydrochloric acid and water. The solution was treated with activated carbon (2.5 % on the expected weight of product) at 50° C. for 1 hour, filtered and the solvent removed under reduced pressure. The light brown oil had an estimated purity of 93.4% and was distilled (boiling range 141°-146° C. at 0.03 mm mercury pressure) to provide a product of 99.8% estimated purity.

The ester was evaluated as an extractant for copper from aqueous solution containing chloride ion using the method of Example 6.

To evaluate the efficiency of the extractant for use with leach solutions containing higher level of total chloride ion, the general test method of Example 6 was repeated using a solution (A) which contained cupric chloride (0.1M), hydrochloric acid (0.1M) and 700 g/l calcium chloride dihydrate, giving a total chloride ion concentration of 9.8M.

The results are displayed in Table 3, and indicate that the extractant is more suitable for use with leach solutions having relatively low total chloride ion concentrations (3.7M), since relatively acid transfer levels occur at high total chloride ion concentrations (9.8M).

EXAMPLE 8

Isooctadecyl nicotinate was prepared using the method of Example 7 from nicotinic acid and a commercial product, isooctadecyl alcohol, obtained from Farbwerke Hoechst AG. The product had an estimated purity 94.5%.

The isooctadecyl alcohol starting material was analysed by capiliary Gas Chromatography and gave traces showing four peaks each of which was approximately the same size. The commercial isooctadecyl alcohol is believed mainly to comprise different geometric isomer of 2,2,4,8,10,10-hexamethyl-5-methylolundecane.

The ester was evaluated as an extractant for copper from aqueous solution containing chloride ion, using the method of Example 7.

The results are displayed in Table 3, and indicate that the extractant is more suitable for use with leach solutions having relatively low total chloride ion concentrations (3.7M), since relatively high acid transfer levels occur at high total chloride ion concentrations (9.8M).

EXAMPLE 9

(2-(n)Hexyldecyl)picolinate was prepared from picolinic acid and 2-(n)hexyldecyl alcohol by the general method of Example 1 with the following differences. The temperature after thionyl chloride addition was maintained at 80° C. for 2 hours and after the esterification reaction, the solution was diluted with petroleum ether 60°-80°, washed with 1M hydrochloric acid and with brine (10 % NaCl). The solvents were removed by evaporation and the dark coloured oil distilled (boiling range 176°-178° C. at 0.07 mm mercury pressure) to give a colourless oil of estimated purity 97.5%.

The ester was evaluated as an extractant for copper from aqueous solutions containing chloride ions by the general method of Examples 6 and 7, except that AROMASOL H was used as solvent. The solution A contained the higher levels of chloride ion (9.8M) indicated in Example 7 and Table 3. Table 3 shows that the extractant is comparatively well suited for operation using leach solutions containing higher levels of total chloride ion since only 9% transfer of hydrochloric acid took place at a total chloride ion concentration of 9.8M.

EXAMPLE 10

Isooctadecyl picolinate was prepared using the method of Example 7 from picolinic acid and isooctadecyl alcohol, the commercial material obtained from Fabwerke Hoechst AG and described in Example 8. The light brown, oily product of the reaction had an estimated purity of 93.5%.

The ester was evaluated as an extractant for copper from aqueous solutions containing chloride ion using the method of Example 7, except that AROMASOL H was used as solvent.

The results are displayed in Table 3, and show that whilst a relatively low extraction of copper takes place from 3.7M total chloride ion solution, good extraction of copper with relatively low acid transfer takes place from 9.8M total chloride ion solution.

EXAMPLE 11

The bis isodecyl ester of pyridine-3,5-dicarboxylic acid was prepared by the method of Example 1 from pyridine-3,5-dicarboxylic acid and commercial isodecanol (obtained from ICI Petrochemicals Division) using modified amounts of reactants as required by the stoichiometry. Toluene was used as reaction solvent in place of xylene and the temperature was maintained at 80°-82° C. for 4 hours after the thionyl chloride addition. Following the esterification reaction, the solution was cooled, washed with dilute sodium hydroxide solution, 1M hydrochloric acid, 0.5M hydrochloric acid and water. The solution was treated with activated carbon (8% on the expected weight of product), the solvent evaporated at reduced pressure and the residue distilled (boiling range 200°-210° C. at 0.08 mm mercury pressure) to give a product having a estimated purity of 97.5%.

This bis-ester was evaluated as an extractant for copper from aqueous solutions containing chloride ion by the method of Examples 6 and 7.

To evaluate the efficiency of the extractant for use with leach solutions containing both high levels of total chloride ion and high acid levels, the general test method of Examples 6 and 7 was repeated using a solution A which contained cupric chloride (0.1M), hydrochloric acid (1.0M) and calcium chloride dihydrate (700 g/l), giving a total chloride ion concentration of 10.7M.

The results are displayed in Table 3, and show that whilst a relatively low extraction of copper takes place from 3.7M total chloride ion solution, excellent extraction of copper takes place with no acid transfer from solutions containing a total chloride ion concentration of 9.8M, and low acid transfer levels are achieved even when the total chloride ion concentration is 10.7M.

EXAMPLE 12

The bis nonyl ester of pyridine-2,4-dicarboxylic acid was prepared using the method of Example 1 from pyridine-2,4-dicarboxylic acid and commercial nonanol (obtained from ICI Petrochemicals Division and containing predominantly 3,5,5-trimethylhexanol), with modified amounts of reactants as required by the stoichiometry. After the thionyl chloride addition, the temperature was maintained at 84°-85° C. for 2 hours whilst after the esterification reaction the product was isolated as described in Example 7. The boiling range of the product was 200°-210° C. at 0.2 mm mercury pressure and the estimated purity was 100%.

The bis-ester was evaluated as an extractant for copper from aqueous solutions containing chloride by the method of Examples 6 and 11, except that AROMASOL H was used as solvent.

The results are shown in Table 3.

EXAMPLE 13

The bis-isodecyl ester of pyridine 2,5-dicarboxylic acid was prepared using the method of Example 1 from pyridine-2,5-dicarboxylic acid and commercial isodecanol, obtained from ICI Petrochemicals Division, with modified amounts of reactants as required by the stoichiometry. Toluene was used as solvent for the reaction, in place of xylene, and after the thionyl chloride addition the temperature was maintained at 77°-83° C. for 1½ hours. After the esterification reaction the product was isolated as described in Example 7, and had a boiling range of 219°-221° C. at 0.08 mm mercury pressure, and estimated purity of 95.5%.

The bis-ester was evaluated as an extractant for copper from solutions containing chloride by the method of Examples 7 and 11.

The results are displayed in Table 3.

EXAMPLE 14

N,N-Di-(n)-octyl picolinamide was prepared using the method of Example 1 from picolinic acid and di-(n)-octylamine. After the addition of thionyl chloride, the temperature was maintained at 79°-80° C. for 5 hours and then raised to distil excess thionyl chloride and a little xylene. The acid chloride suspension was cooled to 48° C. and the molten amine was added at 48°-74° C. over 10 minutes. The reaction was contained at 90° C. for 4 hours and the dark brown solution was cooled and washed with water to remove acidity. The solution was treated with activated carbon (10% on the expected weight of product), filtered, the solvent evaporated and the dark brown oil distilled. The product had a boiling range of 175°-180° C. at 0.15 mm mercury pressure and was dark coloured. It was purified by dissolving in toluene, treating with activated carbon (10% on expected weight of product) and extracting with 2M sodium hydroxide and water. The toluene was removed by evaporation under reduced pressure to give a mid-brown coloured oil of estimated purity 91%.

The amide was evaluated as an extractant for copper from solutions containing chloride ion as in Examples 6 and 7, except that AROMASOL H was used as solvent.

The results are displayed in Table 3.

TABLE 3

| | Transfer of copper (%) and hydrochloric acid (%) from aqueous solution ||||||
|---|---|---|---|---|---|---|
| | SOLUTION COMPOSITION ||||||
| | HCl 0.1 M |||| HCl 1.0 M ||
| | Calcium chloride 250 g/l Total chloride 3.7 M || Calcium chloride 700 g/l Total chloride 9.8 M || Calcium chloride 700 g/l Total chloride 10.7 ||
| Extractant (Example No.) | Cu | H | Cu | H | Cu | H |
| 6 | 52 | 0 | | | | |
| 7 | 54 | 0 | 77 | 25 | | |
| 8 | 49 | 0 | 74 | 25 | | |
| 9* | | | 73 | 9 | | |

TABLE 3-continued

| Extractant (Example No.) | Transfer of copper (%) and hydrochloric acid (%) from aqueous solution | | | | | |
|---|---|---|---|---|---|---|
| | SOLUTION COMPOSITION | | | | | |
| | HCl 0.1 M | | | | HCl 1.0 M | |
| | Calcium chloride 250 g/l Total chloride 3.7 M | | Calcium chloride 700 g/l Total chloride 9.8 M | | Calcium chloride 700 g/l Total chloride 10.7 | |
| | Cu | H | Cu | H | Cu | H |
| 10* | 20 | 0 | 68 | 7 | | |
| 11 | 22 | 0 | 80 | 0 | 79 | 6 |
| 12* | | | 52 | 0 | 51 | 4 |
| 13 | | | 17 | 0 | 29 | 8 |
| 14* | | | 66 | 21 | | |
| 25* | | | 23 | 3 | | |
| 26* | 66 | 12 | 89 | 22 | | |

ESCAID 100 was used as solvent except for those Examples marked * where the solvent was AROMASOL H.

EXAMPLE 15

A 0.5 molar solution of te extractant of Example 1 in Aromasol H (20 ml) was shaken for 1 minute with an equal volume of a solution containing 37.6 g/l zinc, 3.65 g/l HCl and 65 g/l calcium (all as chlorides) having a total chloride ion concentration of 4.5 molar.

Analysis of the resulting aqueous phase showed that it contained 28.1 g/l zinc, indicating a zinc transfer of 25.3%.

EXAMPLE 16

The solvent extraction circuit described in Example 5 was used to evaluate the extractant of Example 1. The feed was:

| | |
|---|---|
| Copper ($Cu^{2+}$) | 25 g/l |
| Iron ($Fe^{2+}$) | 75 g/l |
| Silver ($Ag^+$) | 0.028 g/l |
| Lead ($Pb^{2+}$) | 1.5 g/l |
| Arsenic ($As^{3+}$) | 0.2 g/l |
| Antimony ($Sb^{3+}$) | 0.10 g/l |
| Mercury ($Hg^+$) | 0.005 g/l |

With the exception of silver, which was added as silver nitrate to facilitate dissolution, the metals were in the form of their chlorides. In addition, the solution contained 1.8 g/l of hydrogen chloride, giving a total chloride ion concentration of 3.5 moles per liter.

The strip solution consisted of an aqueous solution containing 29 g/l copper as cupric chloride, adjusted to pH 1.0 with hydrochloric acid.

The solvent phase comprised 175 g/l (0.5M) of the extractant of Example 1 dissolved in AROMASOL H.

The operating conditions were as described in Example 5, except that the aqueous feed to the first strip mixer-settler was heated, and the stripped organic phase returned to the extraction mixer-settlers was cooled. As a result, the first strip stage operated at an average temperature of 45° C., whilst the second strip stage operated at an average temperature of 34° C. The extraction stages operated at 28° C.

The circuit was operated for 53.5 hours with steady transfer of copper from the aqueous feed solution to the strip solution throughout the period of operation as indicated by analysis of solutions passing through the circuit at the times listed below:

| Time (hours) | $Cu^{2+}$ g/l | | |
|---|---|---|---|
| | Raffinates | Stripped Organic | Pregnant Strip Soln. |
| 12 | 8 | 12 | 45 |
| 40 | 10 | 9 | 49 |
| 45 | 9 | 10 | 43 |
| 53.5 | 8 | 10 | 41 |

During the period of operation, analysis for the minor metals present in the feed gave the following results (g/l):

| | $Ag^+$ | $Pb^{2+}$ | $As^{3+}$ | $Sb^{3+}$ | $Hg^+$ |
|---|---|---|---|---|---|
| Strip solution | 0.001 | 0.015 | 0.004 | 0.010 | 0.0002 |
| Pregnant strip solution | 0.001 | 0.030 | 0.008 | 0.012 | 0.0002 |

By way of comparison, the circuit was operated under identical conditions, except that no heating of the strip circuit was used, and all mixer-settlers operated at ambient temperature (22° C.). No precipitate was observed but a gradual build-up of an oligomeric copper complex species was inferred from copper loadings on the extractant greater than that expected for the species $L_2CuCl_2$, where L represents the extractant. The circuit was operated for 30 hours, and during this period, the concentration of copper in both the raffinate and the stripped organic phase steadily increased as indicated below:

| Time (hours) | Raffinate ($Cu^{2+}$ g/l) | Stripped organic ($Cu^{2+}$ g/l) |
|---|---|---|
| 10 | 10.5 | 11.4 |
| 20 | 13.4 | 13.3 |
| 30 | 15.2 | 15.0 |

EXAMPLE 17

The nicotinic acid ester of 2,2,4,8,10,10-hexamethyl-5-methylolundecane (the latter being derivable from the self condensation of two molecules of

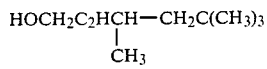

via the Guerbet reaction) was prepared using the method of Example 1. The product had a boiling point of 145° to 150° C. at 0.1 mm pressure and an estimated purity of 90.8%.

The ester was evaluated as an extractant for copper from aqueous solution containing chloride ion using the method of Example 1.

The results are as follows:

| | % |
|---|---|
| Transfer of copper from 0.1 M HCl to B | 42.5 |
| Transfer of copper from 0.1 M HCl to C | 23.6 |
| Transfer of copper from 1.0 M HCl to B | 48.0 |
| Transfer of copper from 1.0 M HCl to C | 30.2 |
| Acid co-extracted from 1.0 M HCl to B | 2.6 |

The acid co-extracted from 0.1M HCL to B was negligible.

EXAMPLES 18 TO 24

The effect of different ester groups on the solubility of a ligand-copper$^{II}$ chloride complex in concentrated solution in a non-polar solvent was examined as follows: Pyridine 3,5-dicarboxylic acid bis esters were prepared by esterifying pyridine 3,5-dicarboxylic acid with a series of different alcohols according to the procedure of Example 11 (see Table 4). Each ester in turn was made up as a 0.5M solution in ESCAID 100 and loaded with copper$^{II}$ chloride (to approximately 75% of the theoretical amount according to the stoichiometry of $L_2CuCl_2$ where L is the bis ester) by shaking with twice its volume of an aqueous solution which was 0.1M in HCl, 0.4M in $CuCl_2$ and which in addition contained 250 g/l of calcium chloride dihydrate. Any separation of the metal ligand complex from the organic solution was noted (Test 1). If no separation occurred, the organic solvent was loaded to approximately 100% of theoretical by shaking with a second aqueous solution which differed from the first only in containing 500 g/l of calcium chloride dihydrate. Again any separation of complex from the organic solution was noted (Test 2). Results are listed below in Table 4.

TABLE 4

| Example | Alcohol used | Test 1 | Test 2 |
|---|---|---|---|
| 18 | Mixed isomer iso-octanol | Immediate precipitation occurred | — |
| 19 | 2-ethylhexanol | Immediate precipitation occurred | — |
| 20 | Commercial nonanol (3,5,5-trimethyl-hexanol) | Immediate precipitation occurred | — |
| 21 | Diisobutyl carbinol | No precipitation | Precipitation occurred after 2 weeks |
| 22 | Mixed isomer isononanol* | No precipitation | No precipitation after 2 weeks |
| 23 | Mixed isomer isodecanol | No precipitation | No precipitation after 2 weeks |
| 24 | Mixed isomer tridecanol | Some precipitation occurred but only after 2 weeks | — |

*The mixed isomer isononanol was obtained by hydroformylation of a mixed octene stream.

The results indicate that the bis esters of Examples 18, 19, 20, 21 and 24 would require to be used in more dilute solution or in a more polar solvent than EXCAID 100, for example a solvent having a higher aromatic content, but that the bis esters of Examples 22 and 23 and their copper complexes have excellent solubility even in concentrated solution in a very weakly polar solvent of low aromatic content.

EXAMPLE 25

N,N,N',N'-tetraisoamyl pyridine-2,5-dicarboxamide was prepared using the method of Example 1 from pyridine-2,5-dicarboxylic acid and diisoamylamine. The crude product in toluene solution was washed several times with 0.5M aqueous sodium hydroxide and then with 0.5M aqueous hydrochloric acid and water. The solution was then treated with charcoal and filtered. The solvent was distilled under reduced pressre, but the product, a brown oil, was not itself distilled. It was made up as a 0.2M solution in AROMASOL H and tested for extraction of copper in the presence of chloride ion using the method of Examples 6 and 7 except that AROMASOL H was used as solvent. The results are given in Table 3. The results indicate that this is a very weak extractant suitable for recovering copper from aqueous solution of high chloride ion concentrations.

EXAMPLE 26

3-hexylundecylamine was prepared from 2-hexyldecanol as follows. The alcohol was heated to 96°–107° and stirred whilst a stream of hydrogen bromide gas was bubbled through it for 4 hours. The organic layer was separated, and washed first with 96% sulphuric acid and then with water, aqueous ammonia until neutral, and water, and then distilled yielding 1-bromo-2-hexyldecane (b.p. 140° at 1 mm pressure). The bromo compound was converted to 1-cyano-2-hexyldecane by stirring it at the reflux temperature with excess of a 44% aqueous solution of sodium cyanide, in the presence of methyl trioctyl ammonium chloride as a phase transfer catalyst, following C. M. Starks (Journal of the American Chemical Society, 93, page 195, 1971). After washing with dilute aqueous sodium hydroxide solution and water, the cyano compound (141 grams) was dissolved in ethanol (130 ml) and poured into an autoclave. Liquid ammonia (150 g) was added and the autoclave was pressurised to 50 atmospheres with hydrogen, sealed, and heated to 170° for 24 hours. The autoclave was cooled, and most of the ammonia allowed to evaporate. The solution was filtered and the solvent was distilled under reduced pressure. It was found by gas chromatography that complete conversion to 3-hexylundecylamine had taken place.

N,N'-bis(3-hexylundecyl)pyridine-2,5-dicarboxamide was prepared using the method of Example 1 from 3-hexylundecylamine and pyridine 2,5-dicarboxylic acid. The product which was a brown oil was not distilled but was analysed as being 92% of theoretical strength (based on MW 642) by titration of an aliquot in acetic acid with perchloric acid. It was made up as a 0.2M solution in AROMASOL H and tested for extraction of copper in the presence of chloride ion using the method of Examples 6 and 7. The results are given in Table 3. They indicated that this compound is a strong extractant for copper which would be best employed in extracting copper from solutions of relatively low chloride ion concentration and relatively low acidity.

EXAMPLE 27

Isohexadecyl-5-bromonicotinate was prepared from 5-bromo nicotinic acid and commercial iso-octadecyl alcohol using the general method of Example 8, except that toluene was used as the solvent in place of xylene. Thus isohexadecyl-5-bromonicotinate (101 parts) was suspended in toluene (240 parts) and dimethyl formamide (1.01 parts) and the suspension stirred and heated to 70° to 80° C. Thionyl chloride (65.45 parts) was added dropwise to the above suspension over about 30 minutes which was then stirred and heated at 70° to 80° C. for a further hour. Excess thionyl chloride was removed by distillation, which also removed a proportion of the toluene. Commercial hexyldecanol (121 parts) was added to the resultant solution over a period of about 30 minutes and the mixture was heated at 70° to 80° C. for a further two hours. The product was isolated by cooling the toluene solution to ambient temperature followed by water washing and distillation to yield 201.4 parts of isohexadecyl-5-bromonicotinate, which had a boiling range of 165° to 175° C. at 0.1 mm mercury pressure.

The ester was evaluated as an extractant for copper as a 0.2 molar solution in SOLVESSO 150, a commercial hydrocarbon solvent of high aromatic content, using the method of Examples 6 and 11. The results are displayed in Table 5, wherein the headings correspond to those of Table 3.

TABLE 5

| | Transfer of copper (%) and hydrochloric acid (%) from aqueous solution | | | | | |
|---|---|---|---|---|---|---|
| | SOLUTION COMPOSITION | | | | | |
| | HCl 0.1 M | | HCl 0.1 M | | HCl 1.0 M | |
| | Calcium chloride 250 g/l | | Calcium chloride 700 g/l | | Calcium chloride 700 g/l | |
| Extractant (Example No.) | Total chloride 3.7 M | | Total chloride 9.8 M | | Total chloride 10.7 M | |
| | Cu | H | Cu | H | Cu | H |
| 27 | — | — | 39 | 0 | 48 | 6 |

We claim:

1. A substituted pyridine which has the formula:

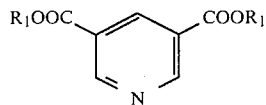

wherein $R_1$ is a hydrocarbyl group containing from 5 to 36 carbon atoms, the two groups $R_1$ may be the same or different and the two groups $R_1$ together contain a total of from 16 to 36 carbon atoms.

2. A substituted pyridine according to claim 1 in which $R_1$ is a mixture of octyl groups derived from mixed isomer iso-octanol.

3. A substituted pyridine as set forth in claim 1 in which $R_1$ is 2-ethyl hexyl.

4. A substituted pyridine as set forth in claim 1 in which $R_1$ is 3,5,5-trimethyl hexyl.

5. A substituted pyridine as set forth in claim 1 in which $R_1$ is diisobutylmethyl.

6. A substituted pyridine as set forth in claim 1 in which $R_1$ is a mixture of nonyl isomers derived from mixed isomer isononanol.

7. A substituted pyridine as set forth in claim 1 in which $R_1$ is a mixture of decyl isomers derived from mixed isomer isodecanol.

8. A substituted pyridine as set forth in claim 1 in which $R_1$ is a mixture of tridecyl isomers derived from mixed isomer tridecanol.

* * * * *